United States Patent [19]

Mao et al.

[11] Patent Number: 5,112,870
[45] Date of Patent: May 12, 1992

[54] BIS(ALKYL-SUBSTITUTED-4-HYDROXY-PHENYLTHIO)ALKANE ANALOGS AS INHIBITORS OF CATARACTOGENESIS

[75] Inventors: Simon J. T. Mao, Loveland; Richard L. Jackson, Cincinnati, both of Ohio

[73] Assignee: Merrell Dow Pharmaceuticals Inc., Cincinnati, Ohio

[21] Appl. No.: 733,505

[22] Filed: Jul. 22, 1991

Related U.S. Application Data

[62] Division of Ser. No. 521,293, May 9, 1990, Pat. No. 5,061,734.

[51] Int. Cl.$^5$ .............................................. A61K 31/10
[52] U.S. Cl. ..................................... 514/712; 514/912
[58] Field of Search ................................ 514/712, 912

Primary Examiner—Frederick E. Waddell
Assistant Examiner—Zohreh A. Fay
Attorney, Agent, or Firm—Louis J. Wille

[57] ABSTRACT

This invention relates to a method of inhibiting the development of a cataract in a patient in need thereof comprising administering to said patient an effective cataract inhibitory amount of a bis(alkyl-substituted-4-hydroxyphenylthio)alkane analog.

2 Claims, No Drawings

BIS(ALKYL-SUBSTITUTED-4-HYDROXY-PHENYLTHIO)ALKANE ANALOGS AS INHIBITORS OF CATARACTOGENESIS

This is a continuation of application Ser. No. 07/521,293, filed May 9, 1990, now U.S. Pat. No. 5,061,734.

BACKGROUND OF THE INVENTION

Oxidative damage to the ocular lens has been recognized as a primary event in the pathogonesis of many forms of cataract. [Augusteyn, R. C. (1981), Protein modification in cataract: Possible oxidative mechanisms. In "Mechanisms of cataract formation in the human lens", (Ed. Duncan, G.) Pp.71-115. Academic Press, Inc., N.Y.] This oxidative damage can be caused by various reactive oxygen species, including $H_2O_2$ and the oxygen free radicals $O_2\cdot^-$ and $HO\cdot$, which are generated in the lens through reduction of molecular oxygen. [Bhuyan and Bhuyan, *Current Eye Research*, 3(1), 67–81 (1984)]. For example, it has been shown that $H_2O_2$ is present in the human eye and is increased in concentration in cataracts. [Bhuyan et al., *I.R.C.S. Med. Sci.* 9, 126–27 (1981); Spector and Garner, *Exp. Eye Res.* 33, 673–81 (1981)].

Oxidative damage can occur through oxidation of crucial sulfhydryl groups of cysteine and methionine amino acids of enzymes and/or membrane proteins. This oxidation can result in inactivation of enzymes and cross-linking of lenticular proteins resulting in the formation of insoluble aggregates of protein which reduce the transparent nature of the lens. For example, senile nuclear cataract formation has been found to be accompanied by a progressive oxidation of cysteine and methionine. [Truscott and Augusteyn, *Biochim. et Biophys. Acta* 492, 43–52 (1977)]. Oxidative damage can also occur through peroxidation of lenticular plasma membrane lipids. It has been shown that there is enhanced lipid peroxidation in human senile cataract. [Bhuyan et al., *I.R.C.S. Med. Sci.* 9, 126–27 (1981); Bhuyan et al., *Invest. Ophthalmol. Vis. Sci.(Supp.)* 18, 97 (Abstr. 4) (1979)]. Peroxidation of plasma membrane lipid can disrupt the physico-chemical properties of the plasma membrane which results in an altered membrane physical characteristics and altered transport function of the membrane.

In the eye, there are two types of natural defenses against the oxidative damage caused by reactive oxygen species, i.e., an enzymatic defense and a nonenzymatic defense. The enzymmatic defense provides protective ocular enzymes, such as superoxide dismutase ($O_2\cdot^-$—:$O_2\cdot^-$ oxidoreductase), catalase ($H_2O_2$:$H_2O_2$ oxidoreductase) and gluthathione peroxidase (GSH:$H_2O_2$ oxidoreductase), which act to reduce the concentrations of reactive oxygen species. These enzymes convert the reactive oxygen species to harmless species, such as water or oxygen, before they can cause oxidative damage to lenticular lipid or protein.

It has been shown that in human senile cataract, cortical activities of the three protective ocular enzymes were markedly decreased. [Bhuyan et al., *I.R.C.S. Med. Sci.* 9, 126–27 (1981)]. It has further been shown that catalase is inhibited by $O_2\cdot^-$ and that his inhibition can be prevented and reversed by superoxide dismutase. [Kono and Fridovich, *J. Biol. Chem.* 257, 5751 (1982)]. Catalase and superoxide dismutase act synergistically in that superoxide dismutase removes the reactive oxygen species $O_2\cdot^-$ thus reducing the concentration of a catalase inhibitor and allowing catalase to operate at a higher activity in removing $H_2O_2$.

The nonenzymatic defense against the oxidative damage caused by reactive oxygen species involves the action of naturally occurring antioxidants such as gluthathione (GSH), ascorbic acid (vitamin C), α-tocopherol (vitamin E) and other biological antioxidants. These naturally occurring agents function by inhibiting the formation of the reactive oxygen species. [Reddan et al., *Exp. Eye Res.* 45, 209–21 (1988)] In particular, *in vitro* and *in vivo* studies in different animal species have demonstrated a significant protective effect of vitamins C and E against light, sugar and steroid induced cataracts. [Gerster, *Z. Ernahrungswiss* 28, 56–75 (1989)].

A number of forms of cataracts exist in man including senile cataracts, which develop in the aged, sugar-induced cataracts, which develop coincidentally with high concentrations of blood sugars such as in galactosemia, and steroid-induced cataracts, which develop due to elevated steroid levels. Guinea pigs fed a high concentration of galactose have been shown to develop cataracts. Kosegarten and Maher [*J. Pharm. Sci.* 67, 1478–79 (1978)] have proposed the galactose-fed guinea pig as a model for galactose-induced cataract formation in man.

It has now been found that certain bis(alkyl-substituted-4-hydroxyphenylthio)alkane analogs inhibit the formation of cataracts. These bis(alkyl-substituted-4-hydroxyphenylthio)alkane analogs which are useful in the method of use of the present invention are compounds of the type disclosed in U.S. Pat. Nos. 3,576,883, 3,786,100, 3,862,332, 3,897,500 and 4,900,757. These compounds include 2,2'-bis(3,5-di-tertiarybutyl-4-hydroxy phenylthio)propane, also known generically as probucol. Probucol is an agent used to reduce total serum cholesterol in man. It has been reported that probucol inhibits oxidative modification of low density lipoprotein [Parthasarathy et al., *J. Clin. Invest.* 77, 641–43 (1986); Carew et al., *Proc. Natl. Acad. Sci. USA* 84, 7725–29 (1987)] and that the antioxidant activity of probucol reduces atherosclerosis in Watanabe rabbits [Mao et al., *International Atherosclerosis Congress*, 53rd Annual Meeting of the European Atherosclerosis Society, Apr. 20–22, 1989, Vienna].

SUMMARY OF THE INVENTION

The present invention provides a method of inhibiting the development of a cataract in a patient in need thereof comprising administering to said patient an effective cataract inhibitory amount of a compound of the formula (1)

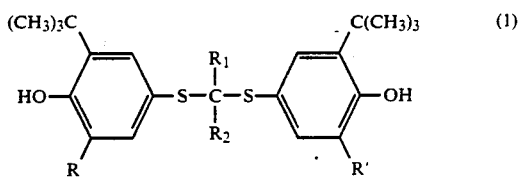

wherein
R and R' are each independently hydrogen or a $C_1$–$C_4$ alkyl;
$R_1$ is hydrogen or methyl; and
$R_2$ is hydrogen or a $C_1$–$C_6$ alkyl,
with the proviso that $R_1$ is methyl when $R_2$ is hydrogen.

The present invention further provides a method of enhancing ocular catalase activity in a patient in need thereof comprising administering to said patient an effective catalase enhancing amount of a compound of formula (1).

DETAILED DESCRIPTION OF THE INVENTION

As used herein the term "$C_1$–$C_4$ alkyl" refers to a saturated hydrocarbyl radical of straight or branched chain configuration of from 1 to 4 carbon atoms. Included within the scope of this term are methyl, ethyl, n-propyl, isopropyl, n-butyl, isobutyl, tertiarybutyl and the like.

The term "$C_1$–$C_6$ alkyl" refers to a saturated hydrocarbyl radical of straight, branched or cyclic configuration of from 1 to 6 carbon atoms. Included within the scope of this term are methyl, ethyl, n-propyl, isopropyl, n-butyl, isobutyl, tertiarybutyl, pentyl, hexyl, cyclohexyl and the like.

Specifically included within the scope of formula (1) is the compound 2,2'-bis(3,5-di-tertiarybutyl-4-hydroxy phenylthio)propane, also known as probucol.

The compounds of formula (1) can be prepared as described in U.S. Pat. Nos. 3,576,883, 3,786,100, 3,862,332, 3,897,500 and 4,900,757. More specifically, 2,2'-bis(3,5-di-tertiarybutyl-4-hydroxyphenylthio)propane can be prepared as described in U.S. Pat. No. 3,576,883. Alternatively, this compound can be prepared according to the method set forth in U.S. Pat. Nos. 4,734,527 (Krauss) or 4,861,443 (Van Effen).

The compounds of formula (1) act to reduce concentrations of reactive oxygen species in the eye and to enhance the activity of the protective ocular enzymes such as catalase. It is believed that by reducing concentrations of reactive oxygen species in the eye such as $O_2\cdot^-$, the compounds of formula (1) remove an inhibitor of catalase and allow catalase to operate at an enhanced activity in removing $H_2O_2$ from the lens. However, the method of use of the present invention is not intended to be limited by a particular theory concerning a possible mechanism of action. The method of use of the present invention encompasses the reduction of concentrations of reactive oxygen species and the enhancement of catalase activity by administration of a compound of formula (1) according to any mechanism by which it might in fact occur.

By reducing concentrations of reactive oxygen species in the eye and by enhancing the activity of catalase, the compounds of formula (1) inhibit the oxidative damage caused by reactive oxygen species to lenticular enzymes, proteins and lipids, and thus inhibit the development of cataracts.

The method of use according to the present invention will be effective in inhibiting those types of cataracts in patients which are induced or exaccerbated by the presence of ocular reactive oxygen species. The types of cataracts for which the present invention would be useful include senile cataract, sugar-induced cataracts, steroid-induced cataracts, age-related cataracts, photochemically induced cataracts, and X-ray and γ-ray induced cataracts.

As used herein, the term "patient" refers to warm-blooded animals or mammals, including humans, who are in need of treatment to inhibit cataract development, such as, for example, in the case of a human suffering from, or in danger of suffering from, a senile cataract, sugar-induced cataract, or steroid-induced cataract condition. The identification of those patients who are in need of treatment to inhibit cataract development is well within the ability and knowledge of one skilled in the art. For example, those patients who upon opthalmological examination exhibit signs of an existing cataract, or who exhibit signs or medical history evidencing an abnormally high risk of developing a cataract, are patients in need of treatment to inhibit cataract development. A clinician skilled in the art can readily identify, by the use of clinical tests, physical examination and medical/family history, those patients who are suffering from a cataract condition and those who are at abnormally high risk of developing a cataract condition. A clinician skilled in the art can thus readily determine if an individual is a patient in need of treatment to inhibit cataract development.

An effective cataract inhibitory amount of a compound of formula (1) is an amount which is effective in lowering the concentration of the reactive oxygen species in the eye and, more specifically, in the ocular lens of a patient. An effective catalase enhancing amount of a compound of formula (1) is an amount which is effective in enhancing ocular catalase activity. According to the present invention, an effective cataract inhibitory amount and an effective catalase enhancing amount of a compound of formula (1) are equivalent. As used herein, the term "effective amount" refers to both an effective cataract inhibitory amount and to an effective catalase enchancing amount of a compound of formula (1).

Successful treatment of a patient is understood to include reducing the levels of reactive oxygen species such as $H_2O_2$ or $O_2\cdot^-$ in the eye or enhancing the activity of the protective ocular enzymes such as catalase, and thereby inhibiting the development of cataracts. Successful treatment is also understood to include prophylaxis in preventing clinically significant development of cataracts in a patient who is at risk of developing cataracts.

In effecting treatment of a patient, the compounds of formula (1) can be administered in any form or mode which makes the compound bioavailable in effective amounts, including oral and parenteral routes. For example, the compound can be administered orally, topically by ophthalmic dosage forms, subcutaneously, intramuscularly, intravenously, transdermally, intranasally, rectally, and the like. Oral administration or topical administration by ophthalmic dosage forms are generally preferred. One skilled in the art of preparing formulations can readily select the proper form and mode of administration depending upon the disease state to be treated, the stage of the disease, and other relevant circumstances.

Where compounds of formula (1) are administered orally, an effective amount will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

Where compounds of formula (1) are administered topically by an ophthalmic dosage form, an effective amount will generally vary from about 10 milligram per kilogram of body weight per day (mg/kg/day) to about 2 grams per kilogram of body weight per day (gm/kg/day). A daily dose of from about 10 mg/kg to about 50 mg/kg is preferred.

The compounds of formula (1) can be administered in the form of pharmaceutical compositions or medicaments which are made by combining the compounds with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose or oral thereapeutic administration, the compounds of formula (1) may be incorporated with excipients and used in the form of tablets, troches, capsules, elixirs, suspensions, syrups, wafers, chewing gums and the like. These preparations should contain at least 4% of the compound of formula (1), the active ingredient, but may be varied depending upon the particular form and may conveniently be between 4% to about 90% of the weight of the unit. The amount of the active ingredient present in compositions is such that a unit dosage form suitable for administration will be obtained. A unit dosage form will typically be administered from 1 to 4 times daily.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel ™, corn starch and the like; lubricants, such as magnesium stearate or Sterotex ™; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

The compounds of formula (1) can also be administered topically by ophthalmic dosage forms such as, for example, ophthalmic drops, ophthalmic ointments, and ophthalmic disks. The ophthalmic drops of the present invention should contain from 0.1-10%w/w of one of the compounds of formula (1). Typically, it will be dissolved in a buffered, isotonic solution containing antimicrobial preservative agents. The ophthalmic ointments will also generally contain from 0.1-10%w/w of one of the compounds of formula (1) admixed with a suitable base, such as white petrolatum and mineral oil, along with antimicrobial preservatives. The ophthalmic disks will typically be constructed so as to contain a core of active ingredient surrounded by a polymer matrix such as, for example, a hydrophobic ethylene/vinyl acetate copolymer. Specific methods of compounding these dosage forms, as well as appropriate ophthalmic pharmaceutical carriers are known in the art. REMINGTON PHARMACEUTICALS SCIENCES, 16th Ed. Mack Publishing Co. (1980).

Typically, ophthalmic drops or ophthalmic ointments will be administered from 1 to 4 times daily. The ophthalmic disks will typically be administered weekly.

For the purpose of oral or parenteral administration, compounds of formula (1) may be incorporated into a solution or suspension. These preparations should contain at least 0.1% of a compound of formula (1), but may be varied to contain between 0.1 and about 50% of the weight thereof. The amount of the active ingredient present in such compositions is such that a suitable dosage will be obtained.

The solutions or suspensions may also include one or more of the following adjuvants: sterile diluents such as water, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The following example illustrates the use of 2,2'-bis(3,5-di-tertiarybutyl-4-hydroxyphenylthio)propane according to the present invention. This example is illustrative only and is not intended to limit the scope of the invention in any way. As used herein, the following terms have the indicated meanings as follows: "mL" refers to milliters, "° C." refers to degrees Celsius, "M" refers to molar concentration, "N" refers to normality, "mM" refers to millimolar concentration, "DTPA" refers to diethylenetriaminepenta-acetic acid, "GSH" refers to reduced glutathione, "NADPH" refers to reduced nicotinamide-adenine dinucleotide phosphat "$\mu L$" refers to microliters, "$\eta m$" refers to nanometers, "MDA" refers to malondialdehyde.

EXAMPLE 1

Effect of 2,2'-Bis(3,5-di-tertiarybutyl-4-hydroxyphenylthio)propane on Ocular Antioxidant Enzyme Activity and Ocular Lipid Peroxides in the Galactose-Fed Guinea Pig Hartley guinea pigs, obtained from Murphy's Breeders Inc. (Plainfield, Ind.), were randomly distributed into one of five treatment groups of five or six guinea pigs each. The guinea pigs were treated as follows:

Group 1—Control (6 animals), fed a diet consisting of normal guinea pig chow 5025 purchased from Purina (Richmond, Ind.);

Group 2—Vitamin C Deficient (5 animals), fed a diet consisting of Vitamin C deficient guinea pig chow supplemented with 15% by weight galactose;

Group 3—Vitamin C Deficient/1% α-tocophorol (6 animals), fed a diet consisting of Vitamin C deficient guinea pig chow supplemented with 15% by weight galactose and 1% by weight α-tocophorol;

Group 4—Vitamin C Deficient/1% probucol (6 animals), fed a diet consisting of Vitamin C deficient guinea pig chow supplemented with 15% by weight galactose and 1% by weight 2,2'-bis(3,5-di-tertiarybutyl-4-hydroxyphenyl thio)propane;

Group 5—Vitamin C Deficient/1% ascorbic acid (6 animals), fed a diet consisting of Vitamin C deficient guinea pig chow supplemented with 15% by weight galactose and 1% by weight ascorbic acid.

The animals were euthanized by administration of carbon dioxide after 4.5 weeks of treatment. After the animals were expired, the eyes were carefully removed and rapidly frozen at −80° C. Ocular lenses were dissected from the eye, weighed and homogenized in 1 mL of 0.05 M phosphate buffer (pH 7.2). The homogenate was centrifuged at 755xg for 20 minutes and the supernatant was collected and evaluated biochemically for levels of catalase activity, glutathione peroxidase activity, malondialdehyde concentration (MDA), and total soluble protein.

Catalase Activity: Catalase activity was measured in an assay system consisting of 10 mM hydrogen peroxide, 50 mM phosphate buffer (pH 7.2) and enzyme extract in 1 mL of phosphate buffer. Catalase activity was measured polarographically using a yellow spring oxygen electrode which quantitates the oxygen generated from the decomposition of hydrogen peroxide by catalase. The electrode was standardized by referencing 0% oxygen to a water solution saturated with 100% nitrogen gas and by referencing 100% oxygen to a water solution saturated with 100% oxygen. The reaction buffer was deaerated with pure nitrogen and placed in a reaction chamber maintained at 37° C. Using microliter amounts of bovine catalase, a standard curve was constructed using slopes along the linear portion of the curves to determine the rate of catalytic activity of catalase. Sample specimens were added to the reaction buffer and slopes for the rates were determined and referenced to the catalase standard curve.

Glutathione peroxidase: Glutathione peroxidase activity was measured by utilizing tertiarybutyl hydrogen peroxide as the substrate. The assay is based on the oxidation of reduced glutathione by glutathione peroxidase coupled to the disappearance of NADPH by glutathione reductase. The enzyme extract was added to the reaction mixture consisting of 0.9 mL of 0.05 M phosphate buffer (pH 7.2) containing 0.5 mM DTPA, 20 μL of 0.1 M GSH, 20 μL of glutathione reductase (50 Units/mL), 20 μL of 8 mM NADPH and 30 mM tertiarybutyl hydrogen peroxide. Samples were incubated at 37° C. for 1 minute and the change in absorbance at 340 ηm was recorded. A standard curve was produced using microliter amounts of glutathione peroxidase. Glutathione peroxidase activity of the samples was determined with reference to the standard curve.

Lipid Peroxides: Lipid peroxide concentrations were determined by treating the lipid peroxides with acid and measuring the concentration of the resulting MDA, which is an acid degradation product of lipid peroxides. 500 μL of sample was added to 0.5 mL of 20% trichloroacitic acid. After a short incubation, 0.5 mL of 0.67% thiobarbituric acid in 0.05 N sodium hydroxide was added and the reaction mixture was incubated at 90° C. for 30 minutes. After centrigugation, 250 μL of supernatant was transferred to a microtiter plate and the absorbance of the sample at 540 ηm was determined.

The results as presented in Table 1 show that treatment of galactose-fed guinea pigs with 2,2'-bis(3,5-ditertiarybutyl-4-hydroxyphenylthio)propane significantly increases activity of ocular antioxidant enzymes and significantly decreases lipid peroxides in the lens.

TABLE 1

Effect of 2,2'-Bis(3,5-di-tertiarybutyl-4-hydroxyphenylthio)propane on Ocular Antioxidant Enzyme Activity and Ocular Lipid Peroxides in the Galactose-Fed Guinea Pig

| Treatment Group | Catalase (units/g wet weight ± S.D.) | GSH Peroxidase (units/g wet weight ± S.D.) | Lipid Peroxides (OD at 540 ηm ± S.D.) |
|---|---|---|---|
| 1. Control | 21.86 ± 8.80 | 2.40 ± 0.69 | 0.054 ± 0.029 |
| 2. Vitamin C Deficient | 14.19 ± 7.61 | 2.32 ± 0.83 | 0.053 ± 0.015 |
| 3. 1% α-tocophorol | 16.07 ± 5.62 | 2.93 ± 0.66* | 0.053 ± 0.015 |
| 4. 1% probucol | 293.14 ± 96.15* | 4.196 ± 0.88* | 0.017 ± 0.008* |
| 5. 1% ascorbic acid | 37.41 ± 8.4 | 2.93 ± 0.65* | 0.031 ± 0.008 |

*p < 0.05 as compared to the Control Group.

As with any group of structurally-related compounds having the same utility, certain compounds of formula (1) are preferred in the method of use according to the present invention. Compounds of formula (1) wherein R and R' are tertiarybutyl are generally preferred. Furthermore, compounds of formula (1) wherein $R_1$ and $R_2$ are methyl are generally preferred. More particularly, the compound 2,2'-bis(3,5-di-tertiarybutyl-4-hydroxyphenylthio)propane is especially preferred in the method of use of the present invention.

What is claimed is:

1. A method of enhancing ocular catalase activity in a patient in need thereof comprising administering to said patient an effective catalase enhancing amount of a compound of the formula

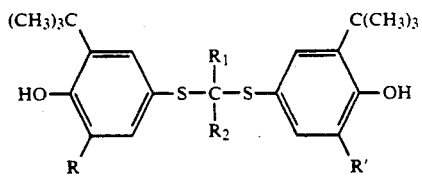

wherein
R and R' are each independently hydrogen, or a $C_1$–$C_4$ alkyl
$R_1$ is hydrogen or methyl; and
$R_2$ is hydrogen or a $C_1$–$C_6$ alkyl,
with the proviso that $R_1$ is methyl when $R_2$ is hydrogen.

2. A method according to claim 1 wherein the compound is 2,2'-bis(3,5-di-tertiarybutyl-4-hydroxyphenylthio)propane.

* * * * *

UNITED STATES PATENT AND TRADEMARK OFFICE
CERTIFICATE OF CORRECTION

PATENT NO. : 5,112,870

DATED : May 12, 1992

INVENTOR(S) : Simon J.T. Mao and Richard L. Jackson

It is certified that error appears in the above-indentified patent and that said Letters Patent is hereby corrected as shown below:

Column 1, line 6 the patent reads: "this is a continuation", and should read --this is a divisional--.

Column 1, line 11 the patent reads: "pathogonesis", and should read --pathogenesis--.

Column 1, line 54 the patent reads: "gluthathione", and should read --glutathione--.

Column 1, line 64 the patent reads: "his", and should read --this--.

Column 4, line 40 the patent reads: "a-patient", and should read --a patient--.

Column 5, line 19 the patent reads: "or oral", and should read --of oral--.

Column 5, line 20 the patent reads: "thereapeutic", and should read --therapeutic--.

Column 6, line 41 the patent reads: "phosphat", and should read --phosphate--.

UNITED STATES PATENT AND TRADEMARK OFFICE
CERTIFICATE OF CORRECTION

PATENT NO. : 5,112,870
DATED : May 12, 1992
INVENTOR(S) : Simon J.T. Mao and Richard L. Jackson It is certified that error appears in the above-indentified patent and that said Letters Patent is hereby corrected as shown below:

```
Column 8, lines 4-5 the patent reads:  "(3,5-ditertiarybutyl-4", and should
read -- (3,5-di-tertiarybutyl-4 --.
```

Signed and Sealed this

Thirteenth Day of September, 1994

Attest:

BRUCE LEHMAN

*Attesting Officer*   *Commissioner of Patents and Trademarks*